United States Patent [19]

Kinney et al.

[11] Patent Number: 4,950,762

[45] Date of Patent: Aug. 21, 1990

[54] 2-PYRIDINECARBOTHIOAMIDES, PROCESSES FOR PREPARATION THEREOF

[75] Inventors: William A. Kinney, Langhorne, Pa.; Amadeo A. Failli, Princeton Junction, N.J.; Ghulam N. Mir, Buckingham, Pa.

[73] Assignee: American Home Products Corporation, New York, N.Y.

[21] Appl. No.: 377,500

[22] Filed: Jul. 10, 1989

Related U.S. Application Data

[62] Division of Ser. No. 123,740, Nov. 23, 1987, Pat. No. 4,886,821.

[30] Foreign Application Priority Data

Jan. 27, 1987 [CA] Canada ............................. 528269
Oct. 27, 1987 [CA] Canada ............................. 550348

[51] Int. Cl.$^5$ ............................................ C07D 211/70
[52] U.S. Cl. ..................................................... 546/313
[58] Field of Search ........................................... 546/313

[56] References Cited

FOREIGN PATENT DOCUMENTS 952635  11/1956  Fed. Rep. of Germany ...... 546/313
3339644  5/1984  Fed. Rep. of Germany ...... 546/313
1121261  4/1981  U.S.S.R. .............................. 546/313

OTHER PUBLICATIONS

CA, vol. 110, 1989, Abs. No. 110; 114,688a.
E. A. Popova et al., Deposited Doc. 1981 SPSTL 586 Khp-D81 (CA 98:50236a).

Primary Examiner—Mary C. Lee
Assistant Examiner—Robert C. Whittenbaugh
Attorney, Agent, or Firm—Walter Patton

[57] ABSTRACT

There are provided gastric antiulcer and cytoprotective substituted N-phenyl-2-pyridinecarbothioamides. The process for their production and formulation is disclosed.

3 Claims, No Drawings

2-PYRIDINECARBOTHIOAMIDES, PROCESSES FOR PREPARATION THEREOF

This is a divisional of co-pending application Ser. No. 07/123,740 filed on Nov. 23, 1987 now U.S. Pat. No. 4,886,821.

BACKGROUND OF THE INVENTION

The present invention relates to novel 2-pyridinecarbothioamides. More particularly, it relates to novel 2-pyridinecarbothioamides which have inhibitory activity on ulcers, to processes for preparation thereof, to pharmaceutical compositions comprising the same, and to the method of using the same therapeutically in the treatment of ulcers in human beings and animals.

The compounds of the present invention have the following formula:

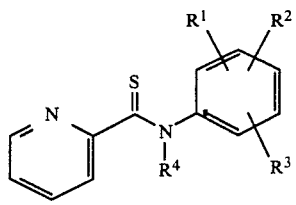

wherein $R^1$ is fluorine, $R^2$ and $R^3$ are each hydrogen or fluorine, and $R^4$ is hydrogen or lower alkyl.

The closest prior art is German Patent No. 953,635 (1956) and E. A. Popova et al, Deposited Doc. 1981, SPSTL 586 Khp-D81. They disclose a number of 2-pyridinecarbothioamides as intermediates in the preparation of therapeutics and bactericidal agents, respectively. However, the compounds of the present invention are not exemplified in the numerous examples contained in the two above mentioned references.

Although the mechanism of cytoprotection is not clearly defined yet, there is a suggestion that it may be partially mediated through the release of gastric mucosal prostaglandins, (Hollander et al, Gastroenterology 86: 1114, 1984 and Tarnawski et al, Gastroenterology 86: 1276, 1984). Szelenyi et al, (Gastroenterology 88: 1604, 1985) has suggested non-prostaglandin mediated mechanisms for cytoprotection.

Activity in the ethanol induced ulcer model is an indication of cytoprotection, regardless of the antisecretory characteristics of the drug. Antisecretory agents, such as the $H_2$ receptor antagonist cimetidine and the anticholinergic agent propantheline bromide do not protect in this model. See Robert et al, Scand. J. Gastroenterol. 19 (Suppl. 101): 69–72, 1984.

The compounds of this invention have been found to possess effective gastric and duodenal cytoprotective properties. These properties along with a relatively low order of toxicity, render these compounds valuable agents for treating ulcers in humans and animals.

SUMMARY OF THE INVENTION

Accordingly, one object of this invention is to provide novel 2-pyridinecarbothioamides which are useful as a medicine for ulcers.

Another object of this invention is to provide processes for the preparation of said 2-pyridinecarbothioamides.

A further object of this invention is to provide pharmaceutical compositions comprising, as an active agent, said 2-pyridinecarbothioamides.

A still further object of this invention is to provide a method of using said 2-pyridinecarbothioamides in the treatment of ulcers in human beings and animals.

DETAILS OF THE INVENTION

We have demonstrated that the 2-pyridinecarbothioamides of the present invention inhibit ethanol-induced ulcers in rats. The activity of said compounds in this test suggests therefore that they possess gastric and duodenal cytoprotective properties. Because of their cytoprotective nature they may be used to treat or prevent disease states such as regional iletis, Crohn's disease, erosive gastritis, erosive esophagitis, inflammatory bowel disease and ethanol-induced hemorrhagic erosions.

For therapeutic purposes, the compounds according to the present invention can be used in pharmaceutical preparations containing said compounds as an active ingredient, in admixture with a pharmaceutically acceptable carrier such as an organic or inorganic solid or liquid excipient suitable for oral or parenteral administration. The pharmaceutical preparations may be capsules, tablets, dragees, solutions, suspensions, emulsions, and the like. If desired, there may be included in the above preparations auxiliary substances, stabilizing agents, wetting or emulsifying agents, buffers and other commonly used additives.

While the dosage of the compounds will vary depending upon the age and condition of the patient, an average single dose of about 1 to 100 mg/kg of the compounds according to the present invention may be effective for treating ulcer. In general, amounts between 1 to 10 mg/kg and preferably about 1.2 mg/kg may be administered per day.

The 2-pyridinecarbothioamides of this invention are novel and can be represented by the following general formula (I):

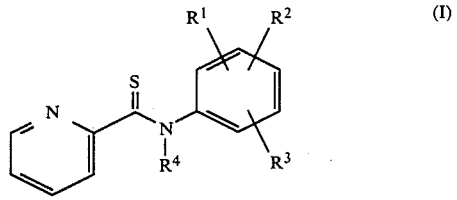

wherein $R^1$ is fluorine, $R^2$ and $R^3$ are each hydrogen or fluorine, and $R^4$ is hydrogen or lower alkyl containing 1 to 6 carbon atoms.

The preferred compounds of the present invention are represented by the structural formula (I) wherein $R^1$ is fluorine, $R^2$ and $R^3$ are each hydrogen or fluorine, and $R^4$ is hydrogen, methyl or ethyl.

Further preferred compounds of the present invention are represented by structural formula (I) wherein $R^1$ and $R^2$ are fluorine, $R^3$ and $R^4$ are hydrogen.

The preferred compounds of the present invention are designated:

| Example | |
|---|---|
| 1 | N-(3,5-difluoropheny-2-pyridinecarbothioamide; |
| 2 | N-(2,4-difluorophenyl)-2-pyridinecarbothioamide; |
| 3 | N-(4-fluoropheny)-2-pyridinecarbothioamide; |

| | -continued |
|---|---|
| | Example |
| 4 | N-(3-fluorophenyl)-2-pyridinecarbothioamide; |
| 5 | N-(2-fluorophenyl)-2-pyridinecarbothioamide; |
| 6 | N-(3-fluorophenyl)-N-methyl-2-pyridinecarbothioamide; |
| 7 | N-(3,5-difluorophenyl)-N-methyl-2-pyridinecarbothioamide; |
| 8 | N-(3,5-difluorophenyl)-N-ethyl-2-pyridinecarbothioamide; |
| 9 | N-(2,6-difluorophenyl)-2-pyridinecarbothioamide; |
| 10 | N-(2,3-difluorophenyl)-2-pyridinecarbothioamide; |
| 11 | N-(3,4-difluorophenyl)-2-pyridinecarbothioamide; |
| 12 | N-(2,5-difluorophenyl)-2-pyridinecarbothioamide;and |
| 13 | N-(2,4,6-trifluorophenyl)-2-pyridinecarbothioamide. |

According to this invention, the compounds (I) can be prepared by the following process.

Process 1

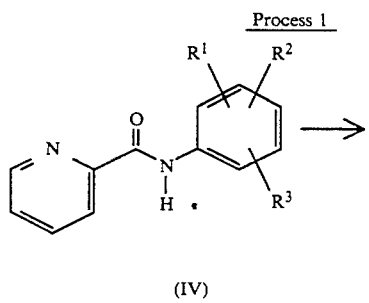

(IV)

wherein $R^1$, $R^2$ and $R^3$ are each as defined above

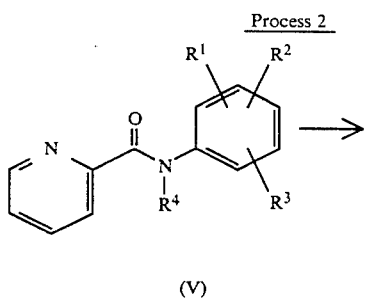

(V)

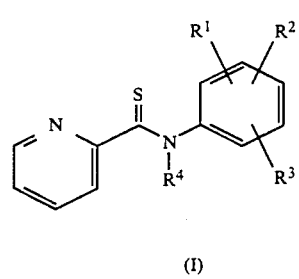

(I)

wherein $R^1$, $R^2$, $R^3$ and $R^4$ are each as defined above.

In the above and subsequent description of the present specification, suitable examples and illustrations for the various definitions to be included within the scope of the invention are explained in detail as follows:

The term "lower" is intended to mean 1 to 6 carbon atoms unless otherwise indicated.

Suitable examples of lower alkyl for $R^4$ may be a straight or branched one such as methyl, ethyl, propyl, isopropyl, butyl, isobutyl, tert-butyl, pentyl, hexyl or the like.

The process for preparing the object compounds (I) are explained in detail in the following.

PROCESS 1

The compounds (I) ($R^4$=—H) can be prepared by reacting a compound (IV) with a thiation agent (e.g. $P_4S_{10}$ or Lawesson's Reagent [2,4-bis(4-methoxyphenyl)-1,3-dithia-2,4-diphosphetane-2,4-disulfide] Tetrahedron Lett., 21, 4061 (1980)).

This reaction is usually carried out in benzene, toluene, xylene or pyridine or any other solvent which does not adversely affect the reaction. The reaction is usually carried out under warming or heating.

PROCESS 2

The compounds (I) ($R^4$=lower alkyl) can be prepared by reacting a compound (V) with a thiation agent (e.g. $P_4S_{10}$ or Lawesson's Reagent) under conditions closely resembling those of Process 1.

The processes for preparing the starting compounds (IV) and (V) are explained in detail in the following.

Process A
Preparation of the compound (IV)

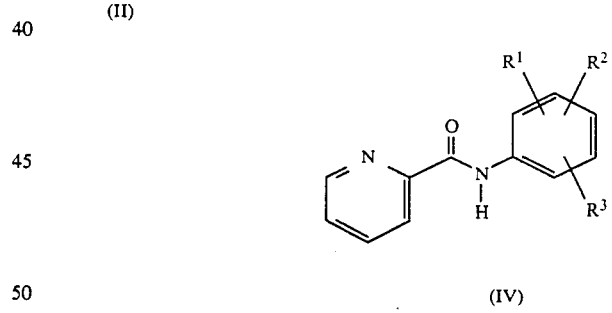

The compound (IV) can be prepared by reacting a compound (II) with a compound (III) or its reactive derivative at the carboxy group. In the above formulas $R^1$, $R^2$ and $R^3$ are each as defined above.

Suitable reactive derivatives at the carboxy group of the compound (III) may include an acid halide, an acid anhydride, an ester, an activated amide, an activated ester and the like.

Suitable examples of such reactive derivatives may be an ester such as lower alkyl ester (e.g. methyl ester, ethyl ester, propyl ester, hexyl ester, etc.), acid chloride, an acid azide, a mixed acid anhydride with an acid such as substituted phosphoric acid (e.g. dialkylphosphoric acid, phenylphosphoric acid, etc.), aliphatic carboxylic acid (e.g. pivalic acid, acetic acid, trichloroacetic acid, etc.) or the like, a symmetrical acid anhydride, an activated amide with imidazole, triazole or dimethylpyrazole, an activated ester with N-hydroxysuccinimide, N-hydroxyphthalimide or 1-hydroxy-6-chlorobenzotriazole, and the like.

When a compound (III) is used in a free acid form the reaction is preferably carried out in the presence of a conventional condensing agent such as N,N'-dicyclohexylcarbodiimide, N,N'-carbonyl-diimidazole, N-cyclohexyl-N'-morpholinoethylcarbodiimide, N-ethyl-N'-(3-dimethylaminopropyl)carbodiimide, thionyl chloride, phosphorus oxychloride, phosphorus oxybromide, oxalyl chloride, lower alkoxycarbonyl halide (e.g. ethyl chloroformate, isobutyl chloroformate, etc.), 1-(p-chlorobenzenesulfonyloxy)-6-chloro-1H-benzotriazole, or the like.

The reaction is usually carried out in a conventional solvent such as dioxane, chloroform, methylene chloride, ethylene chloride, tetrahydrofuran, ethyl acetate, N,N-dimethylformamide, pyridine or any other organic solvent which does not adversely influence the reaction.

The reaction temperature is not critical, and the reaction can be carried out under cooling, at ambient temperature or under warming or heating.

Process B

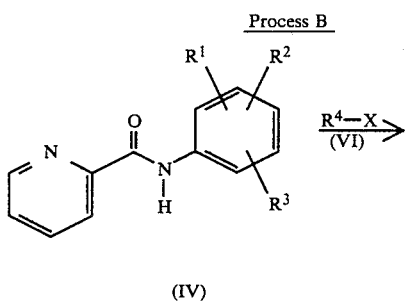

(IV)

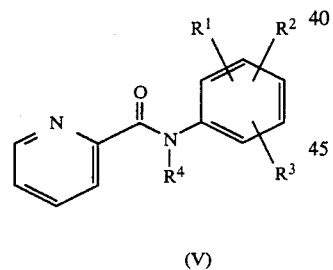

(V)

In the above formulas, $R^1$, $R^2$, $R^3$ and $R^4$ are each as defined above. Suitable examples of the residue X may be halide (e.g. chloride, bromide, iodide) or the like.

This reaction is usually carried out in the presence of a base.

A suitable base may include an inorganic base such as alkali metal anhydride (e.g. sodium hydride, potassium hydride, etc.).

This reaction can be carried out in the presence of a conventional solvent such as aromatic hydrocarbon (e.g. benzene, toluene, xylene, etc.), N,N-dimethylformamide or any other organic solvent that does not adversely influence the reaction.

According to the invention, the compounds (V) wherein $R^4$ is lower alkyl can be prepared by reductive alkylation of the amine (II) with

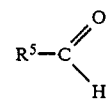

and $Zn(CNBH_3)_2$ to produce the substituted amine

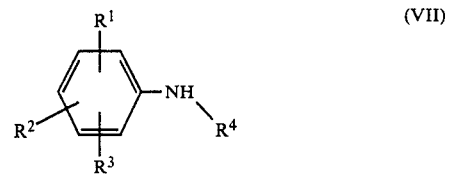

(VII)

wherein $R^5$ is lower alkyl containing one less carbon than $R^4$ and further reacting the substituted amine (VII) with the reactive derivative of (III) to produce the compound (V).

In order to illustrate the usefulness of the compounds of the present invention they were subjected to the following pharmacological assays.

ETHANOL INDUCED CYTOTOXICITY IN RATS

The purpose of this assay is to evaluate the effectiveness of the compounds of the present invention in preventing the formation of gastric musosal lesions produced by ethanol. The assay is based on A. Robert et al: Gastroenterology, 77: 433–443, 1979.

Male Sprague-Dawley rats weighing between 120–150 grams were fasted for 24 hours prior to the experiment (water ad libitum). At least two hours before dosing, the animals were placed in individual cages with wire grid bottoms and denied access to water.

Drug Preparation and Administration

Ethanol was administered orally at 1 mL per animal. The compounds of the present invention were dissolved in water or suspended in water with 0.5% carboxymethylcellulose and administered orally at a dose based on an appropriate standard giving $ED_{50}$ to $ED_{75}$ response of cytoprotective activity.

Methodological Detials

The rats were randomly divided into groups of equal number, ordinarily 10 to a group. The rates were weighed and the individual weights were recorded. Exactly 1 hour (4 hours in the case of Example 5) prior to the administration of ethanol, the screening group was treated with the compounds of the present invention, and the control group with the vehicle. One hour after administering the ethanol the animals were sacrificed by cervical dislocation. The stomachs were removed, cut along the greater curvature and cleansed of all debris with tap water. The stomachs were set aside and kept moist with saline until the lesions were scored.

Sample Analysis

Macroscopic lesions on the gastric mucosa were numerically graded. The final grade assigned a stomach was the sum of all the grades.

| Grade | Description (Approximate length of lesion) |
|---|---|
| 0 | no lesion |
| 1 | 2 mm or less |

| Grade | Description (Approximate length of lesion) |
| --- | --- |
| 2 | 4 mm |
| 3 | 6 mm |

Streaks longer than 6 mm are graded in multiples of 2 mm.

Interpretation of Data

The degree of cytotoxicity occurring in each group is represented as the mean±S.E.M.

Presentation of Results and Criteria for Activity

The mean of each treatment group was compared to the control group and expressed as the % inhibition of lesion formation.

| Example | % Inhibition | Dose mg/kg | $ED_{50}$ mg/kg | m.p. °C. |
| --- | --- | --- | --- | --- |
| 1 | — | — | 1.2 | 140–142 |
| 2 | — | — | 4.8 | 124–129 |
| 3 | — | — | 2.5 | 82–85 |
| 4 | — | — | 1.0 | 72–76 |
| 5 | 69 | 100 | — | 94–97 |
| 6 | 31 | 10 | — | 100–103 |
| 7 | 40 | 25 | — | 131–134 |
| 8 | 13 | 10 | — | 99–101 |
| 9 | — | — | 0.38 | 138–140 |
| 10 | — | — | 1.0 | 89–90 |
| 11 | — | — | 1.6 | 98–100 |
| 12 | — | — | 6.2 | 141–143 |
| 13 | — | — | 0.4 | 160–163 |

STRESS-INDUCED GASTRIC ULCERS IN RATS

The purpose of this assay is to evaluate the effectiveness of the compounds of the present invention in preventing stress induced ulcers.

Male rats (280–380 g) were fasted for 18 hours (water available ad libitum) prior to use in experiments. Eight to twelve rats were used per group.

Drug Preparation and Administration

Drug solutions or suspensions were prepared in physiological saline solution. Suspensions were prepared with the aid of 0.5% carboxymethylcellulose in physiological saline solution. Drugs were administered orally or parenterally at predetermined intervals (usually 15 to 45 minutes) prior to stress.

Methodological Details

This test procedure is according to the method of Senay et al, Proc. Soc. Exp. Biol. Med. 124, 1221 (1967), modified to produce a more consistent ulcer incidence. After drug administration, the rats were immobilized in metallic restrainers and placed in a cold room at 4°–5° C. for 3 hours before they were killed by cervical dislocation. Each rat was given 20 mg of sodium taurocholate p.o. immediately before placing it in the restrainer. After killing the rats, the stomachs were excised and examined. Macroscopic ulcers were subjectively assigned a grade from 1 to 3 on the basis of increasing size. The number of ulcers in each size category was determined and multiplied by the respective grade; the addition of the resultant values gave the cumulative ulcer score. The average cumulative ulcer score of each treatment group was compared to that of the control group and the percent inhibition of ulcer formation was calculated. When the responses obtained were directly proportional to the doses employed, $ED_{50}$ values were determined from the dose-response curves obtained.

| Example | Stress Induced Ulcer $ED_{50}$ mg/kg |
| --- | --- |
| 1 | 0.9 |
| 2 | 38.0 |
| 3 | 3.8 |
| 9 | 1.8 |
| 10 | 0.9 |

The following preparations and examples are given for the purpose of illustrating the present invention.

EXAMPLE 1

N-(3,5-Difluorophenyl)-2-pyridinecarbothioamide
(I, $R^1=3-F$, $R^2=5-F$, $R^3=-H$, $R^4=-H$)

Step (1) Preparation of N-(3,5-Difluorophenyl)-2-pyridinecarboxamide

Picolinic acid (13.0 g, 106 mmol) was added to a solution of 1,1'-carbonyldiimidazole (17.11 g, 106 mmol) in dry dimethylformamide (100 mL) and the reaction stirred for 1 hour, before introduction of 3,5-difluoroaniline (15.0 g, 116 mmol). After 3 days, the reaction mixture was poured into saturated sodium bicarbonate solution (1 L) and extracted with ether (2×500 mL). The organic layers were dried and concentrated to give a solid, which was recrystallized from a mixture of ether and petroleum ether to give N-(3,5-difluorophenyl)-2-pyridinecarboxamide (17.15 g, 69%) m.p. 111°–113° C.

Step (2) Preparation of N-(3,5-Difluorophenyl)-2-pyridinecarbothioamide

N-(3,5-Difluorophenyl)-2-pyridinecarboxamide (7.00 g, 29.9 mmol) was treated with Lawesson's reagent (6.28 g, 15.5 mmol) in toluene (90 mL) at reflux temperature for 4 hours. The solvent was removed, and the residue was dissolved in dichloromethane, preadsorbed onto silica gel, and flash chromatographed (300 g of silica gel eluted with 10% ethyl acetate in petroleum ether). Recrystallization from a mixture of ethyl acetate and hexane afforded N-(3,5-difluorophenyl)-2-pyridinecarbothioamide (3.58 g, 48%) as a yellow solid, m.p. 140°–142° C. Overall yield 33%.

$^1$H NMR (CDCl$_3$, 400 MHz): δ10.86 (br s, NH), 8.75 (d, J=8 Hz, 1H), 8.55 (br d, J=4.5 Hz, 1H), 7.90 (t of d, J=8 and 1.5 Hz, 1H), 7.83 (d of d, J=8.5 and 2 Hz, 2H), 7.52–7.49 (m, 1H), 6.73 (t of t, J=8.5 and 12 Hz, 1H)

UV $\lambda_{max}$(CH$_3$OH): 338 mm (ε9,380), 284.5 (14,500), 235 (15,400)

MS m/z (relative intensity): 250 (M$^+$, 81), 249 (68), 217 (100), 79 (35), 78 (94)

Anal. Calcd. for $C_{12}H_8F_2N_2S$: C, 57.59; H, 3.22; N, 11.20%. Found: C, 57.88; H, 3.33; N, 11.56%.

EXAMPLE 2

N-(2,4-Difluorphenyl)-2-pyridinecarbothioamide (I, $R^1=2-F$, $R^2=4-F$, $R^3=-H$, $R^4=-H$)

Step (1) Preparation of N-(2,4-Difluorophenyl)-2-pyridinecarboxamide

Picolinic acid (10.0 g, 81 mmol) was added to a solution of 1,1'-carbonyldiimidazole (13,13 g, 81 mmol) in dimethylformamide (80 mL) and the reaction mixture was stirred for 1 hour before introduction of 2,4-difluoroaniline (9.06 mL, 89 mmol). After 24 hours, the reaction mixture was poured into saturated sodium bicarbonate solution, extracted into ether, dried, concentrated, and recrystallized using a mixture of ether and petroleum ether to yield N-(2,4-difluorophenyl)-2-pyridine-carboxamide as a white solid (14.37 g, 76.0%) m.p. 90.5°–95° C.

$^1$H NMR (CDCl$_3$, 200 MHz): δ10.21 (br s, NH), 8.63 (br d, J=5 Hz, 1H), 8.6–8.4 (m, 1H), 8.27 (d, J=8 Hz, 1H), 7.92 (t, J=8 Hz, 1H), 7.50 (d of d, J=8 and 5 Hz, 1H), 7.0–6.8 (m, 2H)

Step (2) Preparation of N-(2,4-Difluorophenyl)-2-pyridinecarbothioamide

Lawesson's reagent (29.8 g, 74 mmol) and N-(2,4-difluorophenyl)-2-pyridinecarboxamide (14.37 g, 61 mmol) were combined in toluene (185 mL) and refluxed for 3 hours. After evaporation of the solvent, the residue was dissolved in dichloromethane, preadsorbed on silica gel, and flash chromatographed (eluted with 2% acetate in petroleum ether) to provide N-(2,4-difluorophenyl)-2-pyridinecarbothioamide as a yellow solid (14.45 g, 94%) m.p. 124°–129° C.

$^1$H NMR (CDCl$_3$, 400 MHz): δ10.89 (br s, NH), 8.92 (m, 1H), 8.75 (d, J=8 Hz, 1H), 8.57 (br d, J=5 Hz, 1H), 7.89 (br t, J=8 Hz, 1H), 7.49 (d of d, J=8 and 5 Hz, 1H), 7.02–6.94 (m, 2H)

MS m/z (relative intensity): 250 (M$^+$, 62), 231 (76), 230 (36), 217 (79), 78 (100)

Anal. Calcd. for C$_{12}$H$_8$F$_2$N$_2$S: C, 57.59; H, 3.22; N, 11.19%. Found: C, 57.96; H, 3.41; N, 11.15%.

EXAMPLE 3

N-(4-Fluorophenyl)-2-pyridinecarbothioamide (I, R$^1$=4—F, R$^2$=—H, R$^3$=—H, R$^4$=—H)

Step (1) Preparation of N-(4-Fluorophenyl)-2-pyridinecarboxamide

An anhydrous solution of 1,1'-carbonyldiimidazole (13.13 g, 81 mmol) in dimethylformamide (80 mL) was treated with picolinic acid (10.0 g, 81 mmol), and after 1 hour 4-fluoroaniline (8.46 mL, 89 mmol) was introduced. After 27 hours the reaction mixture was poured into saturated sodium bicarbonate solution (900 mL) and ether (400 mL). The aqueous layer was extracted again with ether (3×400 mL) and the ethereal layers were dried and concentrated. The crude solid residue was recrystallized from a mixture of ether and petroleum ether to yield N-(4-fluorophenyl)-2-pyridinecarboxamide (11.6 g, 66%) as beige crystals, m.p. 100°–103° C.

$^1$H NMR (CDCl$_3$ 200 MHz): δ10.0 (br s, NH), 8.61 (br d, J=4 Hz, 1H), 8.30 (d, J=8 Hz, 1H), 7.92 (br t, J=8 Hz, 1H), 7.77 (d, J=9 Hz, 1H), 7.73 (d, J=9 Hz, 1H), 7.55–7.45 (m, 1H), 7.10 (d, J=9 Hz, 1H), 7.04 (d, J=9 Hz, 1H)

IR (KBr, cm$^{-1}$): 3340, 1680

MS m/z (relative intensity): 216 (M$^+$, 88), 106 (30), 79 (100), 78 (100)

Step (2) Preparation of N-(4-Fluorophenyl)-2-pyridinecarbothioamide

N-(4-fluorophenyl)-2-pyridinecarboxamide (11.47 g, 53.0 mmol) and Lawesson's reagent (25.75 g, 63.7 mmol) were refluxed in toluene for 6.5 hours, preadsorbed onto silica gel, and flash chromatographed (500 g of silica gel eluted with 15% ethyl acetate in petroleum ether) affording N-(4-fluorophenyl)-2-pyridinecarbothioamide as a yellow solid (6.60 g, 54%) m.p. 82°–85° C.

$^1$H NMR (DMSO, 400 MHz): δ10.75 (br s, NH), 8.68 (br d, J=4 Hz, 1H), 8.53 (d, J=8 Hz, 1H), 8.04 (t of d, J=8 and 2 Hz, 1H), 7.98–7.91 (m, 2H), 7.68–7.64 (m, 1H) 7.33–7.26 (m, 2H)

UV λ$_{max}$(CH$_3$OH): 339 mm (ε7,100), 282.5 (13,130), 232.5 (14,300)

MS m/z (relative intensity): 232 (M$^+$, 77), 231 (57), 199 (100), 78 (74)

Anal. Calcd. for C$_{12}$H$_9$FN$_2$S: C, 62.05; H, 3.90; H, 12.06%. Found: C, 62.21; H, 3.88; N, 12.26%.

EXAMPLE 4

N-(3-Fluorophenyl)-2-pyridinecarbothioamide (I, R$^1$=3—F, R$^2$=—H, R$^3$=—H, R$^4$=—H)

Step (1) Preparation of N-(3-Fluorophenyl-2-pyridinecarboxamide

Picolinic acid (10.0 g, 81 mmol) was added to a solution of 1,1'-carbonyldiimidazole (13.13 g, 81 mmol) in dimethylformamide (80 mL) to form the corresponding imidazolide, which after 1 hour was reacted with 3-fluoroaniline (8.55 mL, 89 mmol) at room temperature. After 21 hours, the reaction mixture was poured into saturated sodium carbonate solution (900 mL), extracted into diethyl ether (3×400 mL), dried, concentrated, and recrystallized from a mixture of ether and petroleum ether to afford N-(3-fluorophenyl)-2-pyridinecarboxamide as beige crystals (13.0 g, 74%) m.p. 74°–78° C.

$^1$H NMR (CDCl$_3$, 200 MHz): δ10.06 (br s, NH), 8.60 (br d, J=5 Hz, 1H), 8.29 (d, J=8 Hz, 1H), 7.90 (br t, J=8 Hz, 1H), 7.74 (br d, J=10 Hz, 1H), 7.6–7.3 (m, 3H), 6.83 (br t, J=8 Hz, 1H)

Step (2) Preparation of N-(3-Fluorophenyl)-2-pyridinecarbothioamide

N-(3-fluorophenyl)-2-pyridinecarboxamide (13.0 g, 60 mmol) and Lawesson's reagent (29.2 g, 72 mmol) were refluxed in toluene (180 mL) for 3 hours. The residue obtained after evaporating the solvent was flash chromatographed on silica gel (eluted with 2% ethyl acetate in petroleum ether) and then recrystallized from a mixture of dichloromethane and hexanes to yield a N-(3-fluorophenyl)-2-pyridinecarbothioamide as a yellow solid (6.75 g, 48%) m.p. 72°–76° C.

$^1$H NMR (CDCl$_3$, 400 MHz): δ10.88 (br s, NH), 8.77 (d, J=8 Hz, 1H), 8.54 (br d, J=5 Hz, 1H), 8.19 (d of t, J=8 and 2 Hz, 1H), 7.88 (t of d, J=8 and 2 Hz, 1H), 7.68 (d of d, J=8 and 2 Hz, 1H), 7.48 (d of d of d, J=8,5 and 1 Hz, 1H), 7.42–7.36 (m, 1H), 6.97 (t of d, J=8 and 2.5 Hz, 1H)

MS m/z (relative intensity): 232 (M$^+$, 90), 231 (84), 199 (100), 169 (74), 78 (95)

Anal. Calcd. for C$_{12}$H$_9$FN$_2$S: C, 61.99; H, 3.87; N, 12.05%. Found: C, 62.01; H, 4.01; N, 11.98%.

EXAMPLE 5

N-(2-Fluorophenyl)-2-pyridinecarbothioamide (I, R$^1$=2—F, R$^2$=—H, R$^3$=—H, R$^4$=—H)

Step (1) Preparation of N-(2-Fluorophenyl)-2-pyridinecarboxamide

Picolinic acid (10.0 g, 81 mmol) was added to a solution of 1,1'-carbonyldiimidazole (13.18 g, 81 mmol) in anhydrous dimethylformamide (80 mL), followed by the addition of 2-fluoroaniline (8.6 mL, 89 mmol) 1 hour later. The reaction mixture was poured into saturated sodium bicarbonate solution (900 mL) after 26 hours, and extracted with ether (3×400 mL). The dried organic material was concentrated in vacuo and recrystallized from a mixture of ether and petroleum ether to yield N-(2-fluorophenyl)-2-pyridinecarboxamide as a white solid (11.81 g) m.p. 112°–115° C.

Step (2) Preparation of N-(2-Fluorophenyl)-2-pyridinecarbothioamide

N-(2-fluorophenyl)-2-pyridinecarboxamide (11.81 g, 55 mmol) was reacted with Lawesson's reagent (26.04 g, 64 mmol) in toluene (160 mL) at reflux temperature for 5 hours. The solution was preadsorbed onto silica gel and flash chromatographed (eluted with 2.5% ethyl acetate in petroleum ether) to give N-(2-fluorophenyl)-2-pyridinecarbothioamide as a yellow solid (7.26 g, 39%) m.p. 94°–97° C.

$^1$H NMR (CDCl$_3$, 400 MHz): δ10.74 (br s, NH), 9.07–9.03 (m, 1H), 8.77 (d, J=8 Hz, 1H), 8.58 (br d, J=5.5 Hz, 1H), 7.89 (t of d, J=8 and 2 Hz, 1H), 7.50–7.47 (m, 1H), 7.27–7.19 (m, 3H)

Anal. Calcd. for C$_{12}$H$_9$FN$_2$S: C, 62.05; H, 390; N, 12.06%. Found: C, 61.78; H, 4.17; N, 12.37%.

EXAMPLE 6

N-(3-Fluorophenyl)-N-methyl-2-pyridinecarbothioamide (I, R$^1$=3—F, R$^2$=—H, R$^3$=—H, R$^4$=—CH$_3$)

Step (1) Preparation of N-(3-Fluorophenyl)-N-methyl-2-pyridinecarboxamide.

To a suspension of 60% sodium hydride (1.76 g, 44 mmol) in dry dimethylformamide (50 mL) under nitrogen was added dropwise a solution of N-(3-fluorophenyl)-2-pyridinecarboxamide (6.87 g, 32 mmol), prepared by the process of Example 4, Step 1, in dimethylformamide (25 mL) over 30 minutes. After 30 minutes more, iodomethane (3.58 mL, 57 mmol) was added. The reaction mixture was quenched with water (500 mL), extracted with ether (3×400 mL) and further extracted with ethyl acetate (300 mL). After washing with brine the ethyl acetate layer was combined with the other organic extracts, which were dried and preadsorbed onto silica gel. Flash chromatography (250 g of silica gel gradient elution with 20–50% ethyl acetate in petroleum ether) was utilized to afford N-(3-fluorophenyl)-N-methyl-2-pyridinecarboxamide (3.81 g, 52%) m.p. 75°–78° C.

$^1$H NMR (CDCl$_3$, 400 MHz): δ8.33 (br d, J=5 Hz, 1H), 7.64 (br t, J=7.5 Hz, 1H), 7.52 (d, J=7.5 Hz, 1H), 7.18–7.11 (m, 2H), 6.84–6.80 (m, 3H), 3.49 (s, 3H)

IR (KBr, cm$^{-1}$): 1640

MS m/z (relative intensity: 230 (M+, 78), 124 (67), 107 (28), 79 (83), 78 (100)

Step (2) Preparation of N-(3-Fluorophenyl)-N-methyl-2-pyridinecarbothioamide

Lawesson's reagent (3.20 g, 7.9 mmol) and N-(3-fluorophenyl)-N-methyl-2-pyridinecarboxamide (3.51 g, 15.2 mmol) were heated to reflux in toluene (45 mL) under nitrogen for 2 hours. The residue, after evaporation of the solvent, was dissolved in dichloromethane, preadsorbed onto silica gel, and flash chromatographed (250 g of silica gel eluted with 10% ethyl acetate in petroleum ether) to yield N-(3-fluorophenyl)-N-methyl-2-pyridinecarbothioamide, as a yellow solid (1.70 g, 45%), m.p. 100°–103° C.

$^1$H NMR (DMSO, 499 MHz): δ8.15 (br d, J=4.5 Hz, 1H), 7.67 (t of d, J=8 and 1.5 Hz, 1H), 7.50 (d, J=8 Hz, 1H), 7.24–7.10 (m, 3H), 7.02–6.94 (m, 2H), 3.84 (s, 3H)

MS m/z (relative intensity): 246 (M+, 32), 123 (100), 119 (70), 78 (30)

Anal. Calcd. for C$_{13}$H$_{11}$FN$_2$S: C, 63.39; H, 4.50; N, 11.37%. Found: C, 63.41; H, 4.54; N, 11.38%.

EXAMPLE 7

N-(3,5-Difluorophenyl)-N-methyl-2-pyridinecarbothioamide (I, R$^1$=3—F, R$^2$=5—F, R$^3$=—H, R$^4$=—CH$_3$)

To a suspension of 80% sodium hydride (1.22 g, 41 mmol) in anhydrous dimethylformamide (90 mL), was added dropwise a solution of N-(3,5-difluorophenyl)-2-pyridinecarboxamide, prepared by a process of Example 1, difluorophenyl)-2-pyridinecarboxamide, prepared by the process of Example 1, Step 1 (8.71 g, 37 mmol) in dimethylformamide (30 mL). The reaction mixture was warmed to 65° C. for 1 hour and then treated with iodomethane (2.60 mL, 42 mmol) at room temperature. After 2.5 hours the reaction mixture was poured into water (500 mL) and extracted with ethyl acetate (2×300 mL). The combined organic layers were washed with 75% brine, dried, preadsorbed onto silica gel, and flash chromatographed (300 g, elution with 40% ethyl acetate in petroleum ether) to yield pure N-(3,5-difluorophenyl)-N-methyl-2-pyridinecarboxamide (5.16 g, 21 mmol, 56%, m.p. 102°–104° C.), which was reacted with Lawesson's reagent (4.36 g, 11 mmol) in anhydrous toluene (65 mL) at reflux temperature for 1.5 hours. The toluene was evaporated and the residue was dissolved in dichloromethane, preadsorbed onto silica gel, flash chromatographed (300 g, elution with 10% ethyl acetate in petroleum ether), and recrystalized from ethyl acetate in petroleum ether to afford a yellow solid (2.36 g, 24%), m.p. 131°–134° C.

$^1$H NMR (CDCl$_3$, 400 MHz): δ8.25 (br s, 1H), 7.60 (br s, 2H), 7.09 (br s, 1H), 6.63 (br s, 3H), 3.89 (br s, 3H)

IR (KBr, cm$^{-1}$): 1600, 1110

MS m/z: 264 (M+, 19), 123 (100), 119 (41), 78 (26)

Anal. Calcd. for C$_{13}$H$_{10}$F$_2$N$_2$S: C, 59.07; H, 3.81; N, 10.60%. Found: C, 59.17; H, 4.04; N, 10.73%.

EXAMPLE 8

N-(3,5-Difluorophenyl)-N-ethyl-2-pyridinecarbothioamide (I, R$^1$=3—F, R$^2$=5—F, R$^3$=—H, R$^4$=—C$_2$H$_5$)

Step (1) Preparation of N-(3,5-Difluorophenyl)-N-ethyl-2-pyridinecarboxamide

To a solution of 3,5-difluoroaniline (4.79 g, 37.1 mmol) in methanol (100 mL) at 0° C. under nitrogen, was added acetaldehyde (2.5 mL, 44.5 mmol). After 15 minutes of stirring, a 0.5M solution of zinc cyanoborohydride in methanol (90 mL, 45 mmol) was introduced. The ice bath was removed after 15 minutes and the reaction mixture was stirred at room temperature for 2.5 hours and filtered through celite. Methanol was removed and the residue was dissolved in methylene chloride (400 mL), washed with water (2×200 mL) and brine (400 mL), dried over magnesium sulfate, and concentrated to give a colorless liquid (5.11 g, 32.5 mmol, 88%). The aniline was dissolved in dry methylene chloride (200 mL) and cooled to 0° C. Triethylamine (14 mL, 97.5 mmol) and picolinic acid chloride hydrochloride (6.20 g, 35.8 mmol) were added to the reaction mixture successively. After stirring for 1 hour at 0° C., the reaction mixture was poured into water (1 L), basified using 1N sodium hydroxide solution, and extracted with methylene chloride (3×300 mL). The organic layer was washed with brine, dried over magnesium sulfate, and preadsorbed onto silica gel. Flash chromatogaphy (3 in, elution with 5% methanol in methylene chloride) afforded the amide (5.2 g), which was recrystallized from ethyl acetate in petroleum ether to give a pure tan solid (4.0 g, 41%), m.p. 99°-101° C.

$^1$H NMR (CDCl$_3$, 400 MHz): δ8.36 (br d, J=4 Hz, 1H), 7.69 (t of d, J=8 and 2 Hz, 1H, 7.59 (d, J=8 Hz, 1H), 7.21 (m, 1H), 6.64-6.60 (m, 3H), 3.97 (q, J=7 Hz, 2H), 1.25 (t, J=7 Hz, 3H)

MS (m/z): 262 (M+, 29), 156 (100), 140 (29), 113 (30), 106 (18), 79 (61), 78 (91)

Step (2) Preparation of N-(3,5-Difluorophenyl)-N-ethyl-2-pyridinecarbothioamide

N-(3,5-Difluorophenyl)-N-ethyl-2-pyridinecarboxamide (4.00 g, 15.3 mmol) was dissolved in anhydrous toluene (100 mL) and treated with Lawesson's reagent (6.20 g, 15.3 mmol). The reaction mixture was refluxed for 1.5 hours, cooled, and preadsorbed onto silica gel. Flash chromatography (3 in, elution with 5% ethyl acetate in petroleum ether) gave the thioamide which was recrystallized from ethyl acetate in petroleum ether to afford a pure yellow solid (1.87 g, 44%), m.p. 111°-113° C.

$^1$H NMR (CDCl$_3$, 400 MHz): δ8.24 (br s, 1H), 7.58 (m, 1H), 7.52 (m, 1H), 7.05 (br s, 1H), 6.63 (m, 3H), 4.48 (m, 2H), 1.37 (m, 3H).

MS (m/z): 278 (M+, 16), 123 (100), 78 (22)

IR (KBr, cm$^{-1}$): 1410

Anal. Calcd. for C$_{14}$H$_{12}$F$_2$N$_2$S: C, 60.42; H, 4.35; N, 10.06%. Found: C, 60.62; H, 4.21; N, 10.03%.

EXAMPLE 9

N-(2,6-Difluorophenyl)-2-pyridinecarbothioamide (I, R$^1$=2—F, R$^2$=6—F, R$^3$=—H, R$^4$=—H)

To a 0° C. solution of 2,6-difluoroaniline (6.80 mL, 63.5 mmol) in dry methylene chloride (200 mL), triethylamine (26 mL, 186.5 mmol) was added, followed by picolinic acid chloride hydrochloride (11.3 g, 63.5 mmol). The reaction mixture was brought to room temperature and stirred for 1.5 hours and then poured into water (1 L). The resulting mixture was basified with 2.5N sodium hydroxide solution and extracted with methylene chloride. The organic layer was washed with brine, dried over magnesium sulfate and concentrated to give a beige solid (9.63 g, 41.2 mmol, 65%, m.p. 95°-98° C.). The amide was treated with Lawesson's reagent (14.85 g, 37 mmol) in anhydrous toluene (120 mL) at reflux temperature for 2 hours. The reaction mixture was adsorbed onto silica gel and flush chromatographed (4 in, elution with 5% ethyl acetate in petroleum ether) to give light yellow crystals (5.91 g, 57%, or 37% overall yield), m.p. 138°-140° C.

$^1$H NMR (CDCl$_3$, 400 MHz): δ11.1 (br s, NH), 8.74 (d, J=8 Hz, 1H), 8.56 (d, J=4 Hz, 1H), 7.88 (t of d, J=8 and 2 Hz, 1H), 7.49 (m, 1H), 7.35 (m, 1H), 7.04 (t,J=9 Hz, 2H)

IR (KBr, cm$^{-1}$): 3220, 1510

MS (m/z): 250 (M+, 80), 231 (100), 217 (74), 78 (94)

Anal. Calcd. for C$_{12}$H$_8$F$_2$N$_2$S: C, 57.59; H, 3.22; N, 11.19%. Found: C, 57.76; H, 3.30; N, 10.84%.

We claim:

1. The process for producing compounds of structural formula (I)

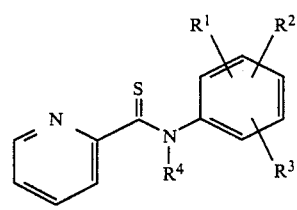

wherein R$^1$ is fluorine, R$^2$ and R$^3$ are each hydrogen or fluorine, and R$^4$ is hydrogen which comprises (a) activating the compound of structure

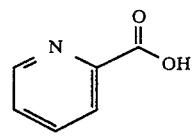

with 1,1'-carbonyldiimidazole to form the activated imidazolide

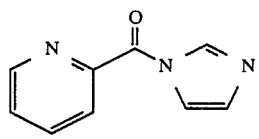

(b) reacting said activated imidazolide with the substituted aniline

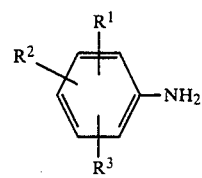

wherein R$^1$, R$^2$ and R$^3$ are as defined above to form the amide

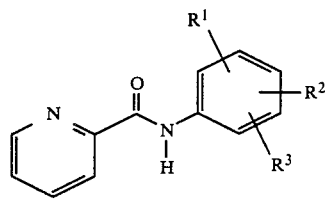

(c) and reacting said amide (IV) with Lawesson's Reagent to form the desired product (I).

2. The process according to claim 1 for producing compounds of structure (I)

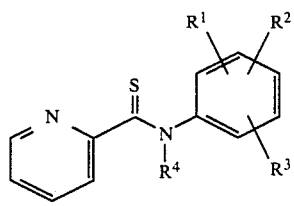

wherein R¹ is fluorine, R² and R³ are each hydrogen or fluorine and R⁴ is lower alkyl containing 1 to 6 carbon atoms which comprises (a) reacting the amide of structure (IV)

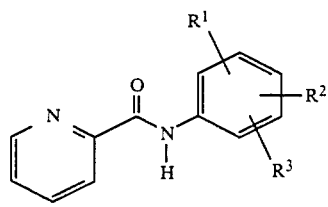

wherein R¹, R² and R³ are as defined above with lower alkyl iodide in the presence of a strong base to form the N-lower alkyl amide of structure (V)

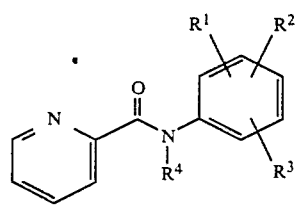

(b) and reacting said N-lower alkyl amide with Lawesson's Reagent to form the desired product (I).

3. The process for producing compounds of structural formula (I)

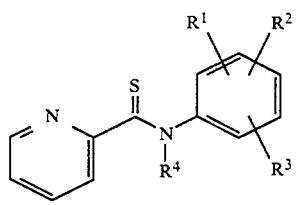

wherein R¹ is fluorine, R² and R³ are each hydrogen or fluorine and R⁴ is lower alkyl containing 1 to 6 carbon atoms which comprises (a) reacting the amine of structure (II)

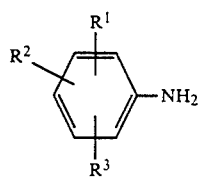

wherein R¹, R² and R³ are as defined above with Zn(CNBH₃)₂ and the aldehyde

wherein R⁵ is lower alkyl containing one less carbon than R⁴ to form the substituted amine of structure (VII)

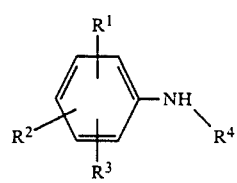

(b) reacting said substituted amine with acid chloride derivative of (III) of structure

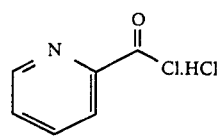

to form the N-lower alkyl amide of structure (V)

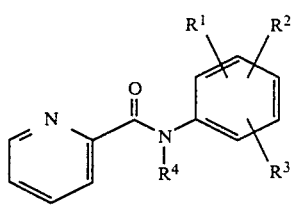

wherein R¹, R², R³ and R⁴ are as defined above, and (c) reacting said N-lower alkyl amide with Lawesson's reagent to form the desired product (I).

* * * * *